US008852866B2

(12) United States Patent
McAlister et al.

(10) Patent No.: US 8,852,866 B2
(45) Date of Patent: Oct. 7, 2014

(54) METHOD FOR PRODUCING AND IDENTIFYING SOLUBLE PROTEIN DOMAINS

(75) Inventors: Mark McAlister, Consleton (GB); Renos Savva, London (GB); Laurence Pearl, London (GB); Chrisostomos Prodromou, Plumstead (GB); Paul C Driscoll, Carshalton (GB)

(73) Assignee: Domainex Limited, London (GB)

( * ) Notice: Subject to any disclaimer, the term of this patent is extended or adjusted under 35 U.S.C. 154(b) by 145 days.

(21) Appl. No.: 10/494,895

(22) PCT Filed: Nov. 8, 2002

(86) PCT No.: PCT/GB02/05075
§ 371 (c)(1),
(2), (4) Date: Sep. 21, 2004

(87) PCT Pub. No.: WO03/040391
PCT Pub. Date: May 15, 2003

(65) Prior Publication Data
US 2005/0019773 A1    Jan. 27, 2005

(30) Foreign Application Priority Data

Nov. 8, 2001  (GB) .................................. 0126887.9

(51) Int. Cl.
| C12Q 1/68 | (2006.01) |
| C12P 19/34 | (2006.01) |
| G01N 33/53 | (2006.01) |
| C12P 21/06 | (2006.01) |

(52) U.S. Cl.
USPC ........... 435/6.12; 435/6.1; 435/91.2; 435/7.1; 435/68.1

(58) Field of Classification Search
USPC .............. 435/6.1, 7.1, 91.2, 68.1, 440, 320.1, 435/6.12
See application file for complete search history.

(56) References Cited

U.S. PATENT DOCUMENTS

| 5,658,754 | A | * | 8/1997 | Kawasaki | 435/69.1 |
| 5,926,641 | A | * | 7/1999 | Shay | 713/320 |
| 6,117,679 | A | * | 9/2000 | Stemmer | 435/440 |
| 6,187,575 | B1 | | 2/2001 | Sobek et al. | |
| 6,190,865 | B1 | | 2/2001 | Jendrisak et al. | |
| 6,291,242 | B1 | | 9/2001 | Stemmer | |
| 6,994,982 | B1 | * | 2/2006 | Watt et al. | 435/7.37 |
| 7,785,828 | B1 | * | 8/2010 | Wu et al. | 435/69.1 |
| 2001/0039014 | A1 | * | 11/2001 | Bass et al. | 435/6 |
| 2001/0044111 | A1 | * | 11/2001 | Carr et al. | 435/6 |

FOREIGN PATENT DOCUMENTS

| WO | 97/12061 | 4/1997 |
| WO | WO 99/54501 A | 10/1999 |

OTHER PUBLICATIONS

Pryor et al., Protein Expression and Purification. vol. 10: 309-319. 1997.*
Cull et al., Methods in Enzymology. vol. 182: 147-153; 1990.*
Muller et al., Analytical Biochemistry. vol. 259: 54-61; 1998.*
Lehninger et al., Principles of Biochemistry. 2nd ed., New York, 1993; p. 985 only.*
Lehninger, "Biochemistry" (1970), title pages and p. 718.*
Cohen, S.L., "Domain elucidation by mass spectrometry", Structure 4 (9), 1013-1016, 1996.
Finucane, M.D., et al., "Core-Directed Protein Design. I. An Experimental Method for Selecting Stable Proteins from Combinatorial Libraries", Biochemistry, vol. 38: p. 11604-11612 (1999).
Kawasaki, M., et al., "Random PCR-Based Screening for Soluble Domains Using Green Fluorescent Protein", Biochemical and Biophysical Research Communications, vol. 280: p. 842-844 (2001).
Moriki, T., et al., "Protein Domain Mapping by λ Phage Display: The Minimal Lactose-Binding Domain of Galectin-3", Biochemical and Biophysical Research Communications, vol. 265: p. 291-296, (1999).
Sambrook, J., et al., "Other Enzymes Used in Molecular Cloning", Molecular Cloning: A Laboratory Manual, $2^{nd}$ ed. p. 5.33-5.86 (1989).
Savva, R., et al., "The structural basis of specific base-excision repair by uracil-DNA glycosylase", Nature, vol. 373: p. 487-493, (1995).
Savva, R., et al., "Nucleotide mimicry in the crystal structure of the uracil-DNA glycosylase-uracil glycosylase inhibitor protein comlex", Nature Structural Biology, vol. 2: p. 752-757, (1995).
Panayotou, G., et al, "Direct Measurement of the Substrate Preference of Uracil-DNA Glycosylase", J. Biol. Chem., vol. 273: p. 45-50, (1998).
Barrett, T.E., et al., "Crystal Structure of a G:T/U Mismatch-Specific DNA Glycosylase: Mismatch Recognition by Complementary-Strand Interactions", Cell, vol. 92: p. 117-129, (1998).
Barrett, T.E., et al, "Crystal Structure of a thwarted mismatch glycosylase DNA repair complex", EMBO Journal, vol. 18: p. 6599-6609, (1999).
Greagg, M.A., et al., "A read-ahead function in archaeal DNA polymerases detects promutagenic template-strand uracil", Proc. Natl. Acad. Sci. USA, vol. 96: p. 9045-9050, (1999).
Bailly, V., et al., "The multiple activities of *Escherichia coli* endonuclease IV and the extreme lability of 5'-terminal base-free deoxyribose 5-phosphates", Biochem. J., vol. 259: p. 761-768, (1989).

(Continued)

*Primary Examiner* — Ardin Marschel
(74) *Attorney, Agent, or Firm* — Kathleen D. Rigaut; Robert C. Netter; Dann, Dorfman, Herrell & Skillman (57) ABSTRACT

Methods for producing and identifying fragments of proteins, and more particularly to methods for generating and identifying soluble protein domains are disclosed based on a method for generating a library of nucleic acid fragments from nucleic acid encoding a desired polypeptide, and more especially a library of essentially, randomly sampled fragments of coding DNA sequence predominantly of defined size range and a method for selecting cloned gene fragments from the library that encode soluble protein domains.

27 Claims, 6 Drawing Sheets

(56) References Cited

OTHER PUBLICATIONS

Wigley, W.C., et al., "Protein solubility and folding monitored in vivo by structural complementation of a genetic marker protein", Nature Biotechnology, vol. 19: p. 131-136, (2001).

Knaust, R.K., et al., "Screening for soluable expression of recombinant proteins in a 96-well format", Analytical Biobhemistry, vol. 297: p. 79-85 (2001).

Nygaard, F.B., et al., "Heterologous expression of soluable, active proteins in *Escherichia coli*: the human estrogen receptor hormone-binding domain as paradigm", Protein Expression and Purification, vol. 21: p. 500-509, (2001).

Pryor, K.D., et al., "High-level expression of soluble protein in *Escherichia coli* using a His6-tag and maltose-binding-protein double-affinity fusion system", Protein Expression and Purification, vol. 10: p. 309-319 (1997).

Gentz, R., et al., "Major surface antigen P190 of *Plasmodium falciparum*: detection of common epitopes present in a variety of plasmodia isolates", EMBO J., vol. 7: p. 225-230, (1988).

Lindahl, T., "DNA glycosylases, endonucleases for apurinic/apyrimidinic sites, and base excision-repair", Progress in Nucleic Acid Research and Molecular Biology, Academic Press, US, vol. 22: p. 135-192, (1979).

Hearn, Milton T.W., et al. "Applications of novel affinity cassette methods: use of peptide fusion handles for the purification of recombinant proteins." J. Mol. Recognit. 2001; vol. 14: 323-369, 3 sheets (dated Feb. 8, 2008 and Feb. 26, 2008) showing vol. 14 No. 6 of J. Mol. Recognit. was available online Dec. 20, 2001; Letter dated Feb. 8, 2008 and additional sheet showing vol. 14 No. 6 of J. Mol. Recognit. was available for public use by The British Library Jan. 3, 2002.

Nord, K., et al. "A combinatorial library of an α-helical bacterial receptor domain." Protein Engineering, 8(6): 601-608 (1995).

\* cited by examiner

Lane 1, 1kb markers. Lane 2, 100bp markers. Lane 3, BRCA2 exon 11 PCR product (1% dUTP). Lane 4, eIF2 PCR product (1% dUTP). Lane 5, NS5 PCR product (1% dUTP). Lane 6, p85nic PCR product (1% dUTP).

Lane 1, kb markers. Lane 2, 100bp markers. Lanes 3-5, NS5 PCR products comprising 0,1 and 10% incorporation of dUTP. Lanes 6-8, NS5 PCR products comprising 0, 1 and 10% incorporation of dUTP after application of the UDG, APE and β-elimination steps of the method.

*Fig. 3*

Lane 1, 1 kb markers. Lane 2, 100bp markers. Lane 3, p85nic 1%dUTP PCR product. Lane 4, p85nic 1%dUTP PCR product after application of the fragmentation method

*Lane 1, 1kb markers. Lane 2, 100bp markers. Lane 3-18, EcoRI/BamHI digests of pCRT7-NT-p85nic fragment clones. EcoRI/BamHI double digestion releases the inserts from pCRT7-NT therefore the bands between 300-1200 correspond to p85nic fragment inserts.*

*Lane 1, 1kb markers. Lane 2, 100bp markers. Lane 3-18, EcoRI digests of pCRBlunt-p85nic fragment clones. EcoRI digestion releases the inserts from pCRBlunt therefore the bands between 300-1200 correspond to p85nic fragment inserts.*

Fig. 6

METHOD FOR PRODUCING AND IDENTIFYING SOLUBLE PROTEIN DOMAINS

FIELD OF THE INVENTION

The present invention relates to methods for producing and identifying fragments of proteins, and more particularly fragments which are soluble domains of a protein. The present invention further provides libraries of expression vectors and host cells comprising nucleic acid encoding the protein fragments and libraries of the protein fragments.

BACKGROUND OF THE INVENTION

There are many large soluble, transmembrane and integral membrane multi-domain proteins of intense biomedical interest. These substances are by definition potential drug targets. Structural and functional analyses of these proteins will provide the basis for design of new strategies for therapeutic intervention in disease. High resolution structural study of proteins provides a basis for understanding biological and disease processes at molecular and atomic levels that is often necessary to support rational design or optimisation of new candidate drugs.

Biochemical and functional assays are used in drug discovery programs to identify compounds that interact with proteins in a manner that interferes with the biological function of the protein. These assays require large quantities of soluble protein to allow screening of thousands of compounds from chemical libraries. However, the production of sufficient quantities of these large proteins for detailed functional and structural studies is rarely feasible using existing methods. In the rare cases where sufficient quantities of large multi-domain proteins can be produced, it is seldom possible to obtain the protein crystals that are prerequisite to structural study by X-ray crystallography or other techniques used in the art such as NMR. However, production of soluble fragments of these proteins may allow identification of regions of a protein that are responsible for the biological functions (or malfunctions), and facilitate detailed structural and functional analysis. Production of soluble protein fragments is therefore necessary to allow in-vitro biochemical and structural analyses of multi-domain proteins that cannot be obtained in sufficient quantities in intact form. However, little is known about the domain structure and organisation of many of these large proteins and bio-informatics approaches often do not provide a sufficient basis for rational identification of candidate domains. As a result, identification and expression of domains from many of these large proteins have proved refractory to the established, rational, recombinant protein engineering/expression strategies.

There are currently three main empirical approaches to identification of soluble protein domains: 1) bioinformatics and sequence analysis to estimate the location of domain boundaries of proteins based on sequence similarities with known proteins, 2) proteolytic fragmentation of the intact protein and identification of soluble fragments (REF), and 3) generation of "random" gene fragments, cloning to produce a gene fragment library and expression screening of the library to identify clones expressing soluble, folded protein fragments. Holistically these methods suffer from a number of weaknesses such as: a requirement for quantities of the intact multi-domain protein for fragmentation that often cannot be obtained; failure to isolate gene fragments capable of producing soluble protein domains.

The most commonly used method for identification of minimal protein domains (domain-mapping) involves limited proteolysis of a target protein and identification of proteolytically resistant fragments by mass spectroscopy (e.g. Cohen, S. L. (1996)). This approach is based on the assumption that stable, folded domains are likely to be more resistant to proteolysis than unstructured regions of peptide sequence that are often found between domains. As this approach usually requires a reasonable quantity of highly purified, intact, soluble target protein derived from the native biological source, a large portion of human proteins of biomedical interest cannot be obtained in sufficient quantities. Protein samples are then enzymatically fragmented using various proteases. The molecular masses of the protein fragments generated are then measured by mass spectroscopy and the identity of the fragments may then be confirmed by further fragmentation (i.e. protein sequencing by MS). It is then assumed that protein fragments of around sixty or more amino acids residues in length represent stably folded domains since these portions of the protein appear to have greater resistance to degradation by proteases. This information is then used to design expression vectors for recombinant expression of the soluble domain candidates identified above.

In practice, there are several caveats with this approach that may result in failure to detect individual protein domains. The cleavage specificity of proteases is limited to the peptide bond between certain amino-acid residue types (e.g. trypsin cleaves the peptide bond to the C-terminal side of basic residues). The position of protease cleavage sites is therefore not a function solely of structural context, but also of amino acid sequence context. Thus, if in practice the appropriate amino acid types are not found in a particular inter-domain peptide sequence, then the adjacent domains may not be separated and therefore the individual domains would not identified. In addition, steric hindrance may prevent protease-mediated cleavage of inter-domain peptide sequences that are short in length. Another major caveat of these approaches is that many domains comprise flexible loop regions that may be proteolytically sensitive resulting in cleavage within a domain (i.e. fail to detect the correct boundaries of a domain). Finally, a peptide sequence that corresponds to a soluble, folded proteolytic fragment may not necessarily be capable of autonomous folding and therefore recombinant over-expression of this particular peptide sequence may fail to produce soluble protein of tertiary structural integrity.

A DNA fragmentation based domain-mapping/identification method requires a protocol for generation of DNA fragments from an intact coding sequence in a manner that allows essentially random sampling of all possible fragments of appropriate size range (i.e. of a size capable of coding for a domain ~200-1500 nucleotides). In addition, the fragmentation protocol should ideally be generically reproducible, and must therefore be independent of differences in the properties of particular DNA targets, and produce fragments that are compatible with conventional methods for cloning of DNA into vectors for protein expression. However, none of the existing DNA fragmentation methods fully meet requirements of random sampling, generic reproducibility, often displaying biased sampling and/or requiring optimisation of the method for particular target DNA properties such as DNA chain-length, and/or producing fragments that are incompatible with subsequent cloning applications. This is not surprising as many methods for fragmenting large DNA molecules have been developed for a wide variety of purposes other than protein domain identification.

A DNA fragmentation based domain-mapping/identification method requires a method for cloning of the DNA fragment mixture to produce a library of the gene fragments. A screening assay must then be used to identify clones that produce soluble folded protein fragments. A number of approaches have been developed for generation of libraries of different clones for a range of purposes including: large-scale DNA sequencing projects (e.g. shotgun cloning); selection of mutant proteins with particular enhanced functional properties (e.g. using gene-shuffling or random mutagenesis); and identification of epitopes for monoclonal antibodies by selection from a phage-display peptide library. Established library-based approaches to selection of protein variants or mutants have been recently adapted to identification of domains in large proteins including for example: a) cloning of DNA fragments into a bacteriophage surface-expression vector for expression as fusions with bacteriophage structural proteins (phage-display) using affinity selection as readout; b) cloning of DNA fragments into expression vectors to produce fusions with a reporter gene such as GFP or an antibiotic resistance gene, using fluorescence and antibiotic resistance respectively as readout of recombinant protein solubility in vivo.

Phage display approaches involve enzymatic fragmentation of coding DNA and cloning of these fragments into a bacteriophage surface-expression vector to produce a phage display library of clones expressing different gene fragments on their surface. A method has been described involving shotgun cloning coupled with phage display mapping of functional domains of two streptococcal cell-surface proteins (Jacobson, et al., 1997). A phage-display library may be screened using a number of different approaches such as: target protein specific affinity selection and DNA sequencing of clones to identify the minimal fragment that retains binding affinity (e.g. Moriki et al., 1999); surface immobilisation of phage clones followed by limited proteolysis and washing to identify recombinant bacteriophage clones that are most resistant to proteolysis and are likely to display a fragment that has tertiary structure (Finucane et al., 1999). A limitation of affinity selection methods for screening of fragment libraries is a requirement for knowledge of the binding affinity(s) of the target protein, since this excludes the large number of proteins for which no specific binding or enzymatic activity has yet been established. Screening by limited proteolysis of phage particles adhered to a surface also suffers from the same caveats as other limited proteolysis approaches described above.

"Random PCR" has been used to generate fragments of target coding sequence for screening for soluble domains as fusions with green fluorescent protein (Kawasaki and Inagaki 2001). Caveats with this approach include: "random PCR" is not truly random and will therefore not produce a complete library of all possible gene fragments of the appropriate size range; attachment of GFP to the expressed gene fragment may affect the folding and solubility of particular candidate domains resulting in both false negative and false positive results. An in vivo method for improvement of the solubility of proteins and protein domain constructs has been described involving mutagenesis of target proteins and production of fusions of target proteins with the antibiotic resistance gene chloramphenicol acetyl transferase and selection of clones with enhanced resistance to chloramphenicol (Maxwell et al., 1999). This method has not been used for domain identification. A caveat with this method is that there is only limited discrimination between soluble and insoluble proteins and the method does not select between folded and misfolded soluble fusions. An in vivo structural complementation based assay has been described involving fusions of the alpha fragment of beta-galactosidase with the C-terminus of target proteins so that if the fusion protein proves to be insoluble then interaction with the omega subunit will be prevented resulting in loss of beta-galactosidase activity (Wigley et al., 2001).

In summary, phage-display and fusion protein based methods have the common caveat that attachment of a reporter protein to a test protein is likely to influence the folding and solubility of the test protein in an unpredictable and target protein specific manner. In practice, existing DNA fragmentation approaches are not ideal for protein domain identification methods as none of these fully meet the requirements of random sampling, generic reproducibility and compatibility with subsequent cloning applications. In addition, all existing methods for domain identification including limited proteolysis, gene fragmentation based methods such as phage display and fusion protein based screening methods all have serious limitations. These undoubtedly lead to failure to detect some protein domains and failure to identify the domains or regions of protein that are responsible for biological activities that could become the new targets for therapeutic intervention and drug development.

SUMMARY OF THE INVENTION

Broadly, the present invention relates to methods for producing and identifying fragments of proteins, and more particularly to methods for generating and identifying soluble protein domains. In preferred aspects, the present invention is based on two innovative methods: 1) one relates to a method for generating a library of nucleic acid fragments from nucleic acid encoding a desired polypeptide, and more especially a library of essentially, randomly sampled fragments of coding DNA sequence predominantly of defined size range; and 2) a second relates to a method for selecting cloned gene fragments from the library that encode soluble protein domains.

In preferred embodiments, the present invention provides a holistic empirical method for the preparation and identification of regions of protein sequence that correspond to minimal domains or larger soluble fragments (e.g. several domains) and also permits production of these fragments in a form that is compatible with the structural and functional analyses identified above.

Accordingly, in a first aspect, the present invention provides a method for producing a library of nucleic acid fragments, the nucleic acid fragments encoding one or more portions of a polypeptide, the method comprising:
  amplifying a nucleic acid sequence encoding the polypeptide in the presence of a non-native nucleotide so that the non-native nucleotide is incorporated into an amplified product nucleic acid sequence at a frequency related to the relative amounts of the non-native nucleotide and its corresponding native nucleotide, if present;
  contacting the product nucleic acid sequence with one or more reagents capable of recognising the presence of the non-native nucleotide and cleaving the product nucleic acid sequence or excising the non-native nucleotide, thereby producing nucleic acid sequences encoding fragments of the polypeptide.

In a further aspect, the present invention provides a library of nucleic acid sequences encoding fragments of the polypeptide produced by the methods described herein.

In the present invention, "a non-native nucleotide" is a deoxynucleotide other than deoxyadenine (dA), deoxythymidine (dT), deoxycytosine (dC) or deoxyguanine (dG) that can replace the corresponding native nucleotide and is recognisable by the reagent used to cleave the product nucleic acid sequence or excise the non-native nucleotide from the product nucleic acid sequence. Preferably, the non-native nucleotides are neutral in terms of coding and are non-mutagenic. Examples of non-native nucleotides include uracil which can be used to replace thymidine and 3-methyl adenine which can be used to replace adenine.

Preferably, the amplification of the nucleic acid sequence is carried out using PCR using a non-native deoxynucleotide, either alone or in a mixture of the non-native and native nucleotide.

The starting nucleic acid sequence employed in the method may be a nucleic acid sequence encoding one or more polypeptide(s). In other embodiments, the starting nucleic acid comprises a cDNA or RNA library, or genomic DNA.

Preferably, the method comprises the further step of ligating the nucleic acid sequences encoding fragments of the desired polypeptide sequence into expression vector(s) to provide a library of expression vectors, and the optional further step of transforming host cells with the expression vectors to produce a library of host cells capable of expressing fragments (domains) of the polypeptide.

The method for generating random gene fragments involves random incorporation of a non-native nucleotide into the product nucleic acid sequence, in place of a native nucleotide, at a frequency that is preferably determined by the molar ratio of non-native to native nucleotide used in preparation of the coding sequence. The amplified nucleic acid product is then preferably contacted with a reagent capable of recognising and cleaving the sequence at the non-native nucleotide, for example by using an enzyme such as a DNA glycosylase or endonuclease, which can recognise the presence of the non-native nucleotide and cleave the nucleic acid sequence at or around the non-native nucleic acid sequence. A preferred protocol employs enzyme(s), β-elimination and temperature changes in order to generate DNA fragments derived by essentially unbiased sampling and predominantly of defined size range. The method of the present invention is particularly advantageous as it allows the production of nucleic acid fragments of a size which encode protein domains of the polypeptide, e.g. preferably between 100 and 1500 nucleotides, more preferably between 200 and 1200 nucleotides, and most preferably between 300 and 1000 nucleotides in length, and is capable of fine sampling of the nucleic acid encoding the polypeptide, producing fragments on average every second nucleotide. In order to allow generic application for library sampling of any polypeptide it may be advantageous to re-code certain nucleotide sequences to contain more incorporation sites for the non-native nucleotide, up to the limits imposed by the constraints of the genetic code.

Optionally, the nucleic acid fragments may then be further amplified to produce nucleic acid fragments for further uses. Additionally or alternatively, the nucleic acid fragments may be exposed to enzymes that mediate attachment of the fragments to other DNA molecules, such as an expression vector, comprising sequences responsible for control of transcription and translation of the gene fragments and optionally sequence encoding affinity tag peptide sequences and optionally sequence for replication of the derived DNA constructs in host cells to produce gene fragment expression constructs.

Thus, in a preferred embodiment, the present invention provides a method of producing fragments of a desired polypeptide, the method comprising expressing the nucleic acid sequences encoding fragments of the desired polypeptide and optionally isolating the polypeptide fragments thus produced. Preferably, the polypeptide fragments are expressed as fusions with an affinity tag, so that they can be purified by affinity chromatography. Preferably, peptide based affinity tags will be less than 25 amino acid residues long, and more preferably less than 15 residues long. Preferred affinity tags have minimal effect on the solubility, stability and/or aggregation state of the attached protein fragment. The use of C-terminal affinity tags is preferred as this permits the selection of clones that express in-frame fragments of DNA, while DNA fragments which are out-of-frame would tend to terminate prior to the translation of the tag.

Examples of suitable affinity tags include polyhistidine (e.g. the hexa-His tags exemplified herein) which bind to metal ions such as $Ni^{2+}$ or $Co^{2+}$, Flag or Glu epitopes which bind to anti-Flag antibodies, S-tags which bind to streptavidin, calmodulin binding peptide which binds to calmodulin in the presence of $Ca^{2+}$, and ribonuclease S which binds to aporibonuclease S. Examples of other affinity tags that can be used in accordance with the present invention will be apparent to those skilled in the art.

In a further aspect, the present invention provides a library, e.g. as produced by a method of described herein, which is:
(a) a library of nucleic acid fragments of a parent nucleic acid sequence, wherein the nucleic acid fragments have a size range as disclosed herein and are preferably sampled from the parent nucleic acid sequence on average about every second nucleotide; or
(b) a library of expression vectors which comprise a plurality of the nucleic acid fragments as set out in (a), wherein each fragment is ligated to a nucleic acid sequence encoding an affinity tag and optionally one or more further sequences to direct the expression of the nucleic acid fragment and the affinity tag; or,
(c) a library of host cells transformed with the expression vectors as defined in (b); or
(d) a library of polypeptide fragments produced by expressing the nucleic acid sequences, wherein each polypeptide is coupled to an affinity tag.

Preferably, this method makes use of non-native nucleotides, and in particular non-native nucleotide bases that can be randomly incorporated into the DNA duplex and then selectively excised to produce the nucleic acid fragments of the polypeptide. None of the current enzymatic methods reviewed above, that aim to produce DNA fragments of essentially random distribution with respect to the source DNA (e.g. DNAase 1 digestion), provide robust control of fragment size range or sampling of DNA in a manner fully independent of DNA secondary structure, or robust reproducibility. In contrast, the present method preferably provides fine sampling with cleavage every second nucleotide on average, robust control of fragment size range, rapid and facile execution, and robust reproducibility. The DNA produced by the method is also compatible with blunt ended and TA cloning methods for construction of expression vectors.

In a preferred embodiment, the present invention employs a DNA fragmentation method based upon an enzymatic fragmentation DNA base-excision repair pathway, (Savva, et al., 1995; Savva and Pearl, 1995; Panayotou, et al., 1998; Barrett, et al., 1998; Barrett et al., 1999). This system initiates the removal of uracil the pro-mutagenic deamination product of cytosine from DNA by the sequential hydrolysis of the bond linking the base to the sugar, followed by cleavage of the sugar phosphate backbone at the abasic site by an apurinic/apyrimidinic endonuclease (APE). The initial reaction, catalysed by uracil-DNA glycosylase (UDG) is exquisitely specific for uracil, and proceeds with very high efficiency. Thus, exposure to UDG and APE enzymes produces a single-strand nick in a dsDNA molecule wherever a uracil occurs. Like the normal DNA component thymine (identical to 5-methyl-uracil), uracil forms stable Watson-Crick base pairs with adenine, and can be efficiently introduced into dsDNA by template-dependent DNA polymerase reactions, using Pol 1 family enzymes such as Taq in PCR reactions. The widely used archaeal DNA polymerases such as Pfu or Vent are inhibited by template strand uracil (Greagg et al., 1999) and are not suitable for this purpose. Incorporation of uracil opposite a template-strand adenine occurs with comparable efficiency to incorporation of thymine, and is unbiased by sequence context. Thus, the probability of uracil incorporation in the daughter strand opposite a template-strand adenine is purely a function of the ratio of TTP/dUTP present in the PCR reaction mix and independent of uracil incorporation in previous cycles. The product of an 'ideal' TTP/dUTP PCR reaction is a mixture of otherwise identical double-stranded DNA molecules in which each possible thymine in either strand has been replaced by uracil. PCR under these conditions is robust even for relatively large PCR products. When this reaction mixture is exposed to UDG and APE to completion, single-strand breaks are introduced at each position at which a uracil was incorporated. A typical mammalian genome has a thymine content≈25%, therefore double stranded DNA fragments are generated beginning and ending≈every $2^{nd}$ base since cleavage may occur at uracil sites on both coding and non-coding strands.

Cleavage by APE leaves a deoxyribose phosphate moiety at the 3' or 5' side of the nick, depending on the specificity of the APE used. The deoxyribose phosphate moiety may then be removed by β-elimination, which is accelerated by mild bases such as spermine and elevated temperature (Bailly and Verly, 1989) to produce single nucleotide gaps in one strand of the duplex. In order to produce blunt-ended DNA fragments for cloning two alternative approaches may be used: 1) cleavage of the single-stranded DNA opposite the single-nucleotide gaps in the duplex DNA using S1-nuclease (Vogt, 1973) (FIG. 1); 2) thermal denaturation of the duplex DNA and re-annealing of the DNA at reduced temperature and filling of 3' recesses using a template dependent DNA polymerase, followed by removal of 3' extensions using a single-strand specific exonuclease with 3'-5' exonuclease activity such as Mung bean nuclease or a single-strand specific endonuclease such as S1-nuclease (FIG. 2).

This DNA fragmentation method has several advantages over other possible methods. Firstly, given pure reagent enzymes, every enzymatic step can be allowed to go to completion, so that the size distribution of the fragments generated, is dictated solely by the TTP/dUTP ratio used in the original PCR reaction. This is in contrast to other enzymatic digestion approaches such as: cleavage by endonucleases (eg. DNAase I) that cleave both strands of duplex DNA, which fully degrade DNA to free nucleotides if the digestion is allowed to go to completion. Computer simulations of the present method using a 5120 base pair gene suggest that a TTP/dUTP ratio of 100:1 will give even cover of the coding sequence, and good representation of fragments in the desired 'domain' size range (~300-1000 nucleotides). Secondly, all the procedures involved are enzymatic and therefore carried out under 'mild' conditions that will cause no other DNA damage, and are completely compatible with rapid efficient DNA purification methods such as ion-exchange and silica-based adsorption methods that may be used between subsequent steps. Thirdly, the products of these reactions are fully 'biological' and suitable for cloning into expression vectors by blunt-end ligation or TOPO-isomerase I-mediated ligation.

It would also be possible to employ a different non-native nucleotide and use a corresponding enzyme which is capable of recognising the non-native nucleotide in the amplified nucleic acid sequence and removing it from the amplified nucleic acid sequence or cleaving the sequence, thereby generating the fragments. One example is 3-methyladenine-DNA glycosylase from *E. coli* which is another monospecific DNA glycosylase that could also be used if deoxy-3-methyladenine (3-meA) mononucleotides are incorporated instead of deoxyadenine (both form base pairs with thymidine). This nucleotide could be generated by exposing deoxyadenine mononucleotides to the methylating agent methyl methanesulphonate (MMS) and re-purifying them.

In many circumstances, it will be desirable to generate 'ragged-terminus' libraries in which, for example, a domain such as an N-terminal domain is always present, but a wide range of C-termini are to be sampled. This can be readily achieved using the method by performing two PCR steps and a thermal denaturation and annealing step: 1) amplification of the constant 5'-segment encoding the N-terminus in a TTP PCR reaction; 2) amplification of a 3' segment that partially overlaps with the 5' segment in a TTP/dUTP PCR reaction; 3) and then mixing the products of these two PCR reactions before thermal melting and re-annealing. A restriction endonuclease (RE) site, that generates a "sticky-ended" on cleavage, may be introduced into the 5' extremity of the 5'-segment, so that the library of N-terminally constant but C-terminally ragged coding sequences can then be efficiently cloned into a vector cleaved the above RE and another with a second RE that generates a blunt end.

In a further aspect, the present invention provides a method of identifying soluble protein domains, the method comprising:
  expressing a library of nucleic acid fragments to produce the protein domains encoded by the fragments, wherein the protein domains are expressed as fusions with an affinity tag; and
  separating soluble proteins using the affinity tag.

Examples of affinity tags that can be employed in the present invention are provided above and many others will be apparent to the skilled person. The use of C-terminal affinity tags is preferred as this permits the selection of clones that express in-frame fragments of DNA, while DNA fragments which are out-of-frame would tend to terminate prior to the translation of the tag.

The method may comprise the additional step of identifying soluble proteins which are domains of the polypeptide, e.g. share a binding or biological activity with the full length parent polypeptide.

Optionally, the method comprises making a library of soluble protein fragments or domain and contacting the fragments or domains with one or more candidate compounds to determine whether one or more of the candidate compounds binds to and/or modulates an activity of a protein fragment or domain present in the library. The candidate compounds may be small molecules or alternatively candidate polypeptide binding partners, e.g. the method can be used to investigate ligand-receptor binding, enzyme-substrate binding, antibody-antigen binding, protein-ligand binding or protein-nucleic acid binding. In still further embodiments, two or more libraries of soluble protein fragments or domains can be crossed to determine whether binding or modulation of activity occurs between members of the libraries. By way of example, in this embodiment of the invention, libraries of domains of two proteins can be made to determine which portions of those proteins are involved in binding and biological activity.

In this aspect of the present invention, the nucleic acid fragments is introduced into an expression vector(s) to produce a library of different DNA fragment expression constructs and protein expression is induced and the derived protein then treated in a novel approach that selectively removes insoluble and/or soluble misfolded and/or non-specifically aggregated protein fragments allowing selective detection and purification of the soluble folded unaggregated or specifically aggregated protein fragments.

The approach makes use of the observation that empirically the process of purification of affinity tagged (such as hexahistidine tagged) proteins by affinity chromatography (such as metal affinity chromatography) is strongly selective for soluble, folded proteins. Selection occurs in several stages in the purification method including: loss of insoluble protein at filtration or centrifugation steps; loss of weakly soluble, misfolded or non-specifically aggregated protein by precipitation or non-specific binding to various surfaces such as plastic and glass surfaces at all stages of purification; loss of misfolded or non-specifically aggregated protein by failure to adsorb to affinity media, and/or loss at washing steps. In our studies, affinity tags, such as the hexa-histidine tag, appear to display considerably lower accessibility to affinity chromatographic media when attached to misfolded, aggregated and/or insoluble target proteins, rather than to stably-folded, un-aggregated, soluble target proteins. This selectivity is likely to result in part from differences in the degree of steric hindrance of binding to affinity media, resulting from the properties of the target protein (e.g. soluble vs. insoluble, folded vs. misfolded, non-specifically aggregated vs. un-aggregated or specifically aggregated). In this novel method, the DNA fragment expression library is induced and screened for soluble protein expression on the basis of the selectivity of affinity purification media for binding of folded, soluble tagged proteins over misfolded, insoluble or aggregated tagged proteins.

In some embodiments, the blunt-ended DNA fragments may be operationally linked to DNA sequences such as an expression vector, comprising sequences responsible for control of transcription and translation of the gene fragments and optionally sequence encoding affinity tag peptide sequences and optionally sequences for replication of the derived DNA constructs in host cells.

In some embodiments the library of blunt ended gene fragments are ligated into a suitable expression vector using conventional blunt-ended ligation methods. Alternatively, the blunt-ended gene fragments are cloned into a suitable expression vector. An inducible expression vector may be used such as those based on the pET series in which the restriction fragments can be inserted between the T7 promoter and start codon at the 5' end, and stop-codons and transcription terminator at the 3' end. Different versions of the vector may be constructed, to include an affinity tag (e.g. a $His_6$-tag) and an optional protease cleavage site at the N-terminus or C-terminus of the expressed fragment. A number of different vectors may be employed to provide start and stop codons in all three reading frames. The procedures described here are not limited to the use of the $His_6$-tag, and allow for the use of alternative tags and/or development of alternative short tags compatible with fluorescence or FRET-based protein detection strategies for example. The expression vectors constructed above constitute a gene fragment expression library. This library is then transfected into host cells and the transformed cells then spread on to selection media plates.

Several hundreds or thousands of individual colonies may then be picked from the selection media plates and transferred to multi-well growth plates containing suitable growth medium. Several hundreds or thousands of clones may be analysed, so that all subsequent stages may be processed in parallel utilising multi-well formats implemented on a multi-well plate format liquid-handling robot. Plates are incubated at 15-37° C. overnight, and aliquots transferred into a second plate for growth for 2-3 hours. Optionally, expression may be induced by addition of inducer molecules or temperature change, and cultures grown for a further period post-induction. Alternatively, a constitutive promoter system may be utilised. Cell-growth is monitored by optical density measurement. The cells are then lysed and then contacted with appropriate affinity chromatography media such as metal chelate media in conditions under which insoluble or soluble mis-folded protein molecules are removed by precipitation or adsorption onto surfaces, such that only soluble folded protein fragments are efficiently purified. The purified soluble protein fragments are analysed with respect to concentration and covalent structural integrity.

Preferably, the expressed proteins are released for separation under non-denaturing conditions, e.g. by enzymes, or non-denaturing detergents. Thus, host cells such as induced bacterial cells are lysed using lysozyme and non-denaturing detergents, and the lysates applied to a multi-channel filter system (e.g. Qiagen TurboFilter) that removes unbroken cells, cell debris and insoluble material. Alternatively, the lysates may be clarified by centrifugation. The clarified lysates containing the soluble contents of the induced cells are then purified in parallel in multiwell format by affinity chromatography (e.g. metal affinity chromatography) and assayed by anti-tag immunoblot or ELISA, SDS-PAGE and mass spectrometry and other methods known to those skilled in the art. This combination of readouts guarantees high sensitivity (blot or ELISA), assessment of purity (SDS-PAGE) and validation of the molecular composition, in addition to quantifying the protein expression level. In an alternative configuration of this embodiment, multiple clones are individually picked from the selective media plate and then cultured together in selective liquid media and processed together at all subsequent steps in order to reduce the total number of parallel operations to be performed. The chances of any one fragment of the appropriate size range corresponding to a folded domain and therefore giving a positive readout is likely to be 0.01-1%. In this context, when a pool of clones gives a positive readout then each original clone present in the pool or subpool is reprocessed to identify which clone(s) produced the positive readout.

In a further alternative embodiment, all colonies from the selection media plates may be pooled and cultured in single vessel containing selective liquid media as described above with respect to temperature and induction of expression, before cell lysis and purification by affinity chromatography. In this embodiment, the purified protein mixture is then analysed as described above and is likely to be found to contain multiple soluble protein fragments, which can be identified by protein sequencing and/or by fragmentation mass spectroscopy. The coding DNA sequences corresponding to the protein fragments identified are then amplified by PCR and cloned into expression vectors using established methods known to those skilled in the art and used for large-scale preparation of the protein fragment. In this context different versions of expression vectors may be constructed, to include an affinity tag (e.g. $His_6$-tag) and an optional protease cleavage site at the N-terminus or C-terminus of the expressed fragment.

Once clones that express soluble protein fragments have been identified these clones are then cultured on a larger scale with optional optimisation of expression, and processed as described above, before purification employing the affinity tag, e.g. employing chromatography media and methods well known to those skilled in the art. The purified soluble protein fragments are analysed with respect to concentration, covalent structural integrity, tertiary structural integrity and biological and/or enzymatic activity using methods well known to those in the art.

One embodiment of this method seeks to identify soluble fragments of an extracellular protein or extracellular domains of a transmembrane or integral membrane protein that are suitable for high-level expression and secretion in bacterial systems. In this embodiment, the library of nucleic acid fragments is cloned into an expression vector that fuses a bacterial periplasmic export signal (such as OmpA) and signal peptidase cleavage site to the N-terminus of the expressed protein fragment. An affinity tag can optionally be included following the signal peptidase site or at the C-terminus of the expressed protein fragment. Bacterial colonies expressing these protein fragments are treated with gentle osmotic shock to release proteins from the bacterial periplasmic space, with minimal release of proteins from the cytoplasm. The periplasmic contents and bathing culture medium are then filtered and contacted with affinity resins as in the basic methodology. In this embodiment, only those protein fragments that were efficiently secreted into the periplasmic space, were proteolytically released from the signal peptide, and were soluble and unaggregated following secretion from the cells or after osmotic shock, are efficiently purified and will give strong anti-tag signals in immunoblot or ELISA assays.

A further embodiment of the method seeks to identify candidate surface proteins from bacteria, suitable for vaccine development. In this embodiment, the method for identification of soluble fragments suitable for high-level expression and secretion in bacterial systems described above, is applied to screening a DNA fragment library derived from part of, or an entire bacterial genome, generated by some type of DNA fragmentation method. DNA fragments from such a library will be cloned into the expression vector for periplasmic export, and colonies screened for expression of soluble tagged-protein fragments in culture medium and periplasmic extract. Those expressed protein fragments that give strong anti-tag signals, will be those that were efficiently secreted into the periplasmic space, were proteolyticaly released from the signal peptide, and were soluble and unaggregated. It is most likely that protein fragments that fulfil these criteria efficiently will derive from extracellular proteins, or from the extracellular domains of transmembrane or integral membrane proteins, encoded by the bacterial genome being screened. Such proteins would have a high likelihood of being visible to the immune system of an organism infected by the bacterium being screened, and would therefore be good candidates for vaccine development.

In a further variation, the method can be used to identify stable and soluble complexes formed between fragments of different proteins or between fragments of a single protein. In one embodiment of this variation, two or more DNA fragment libraries are co-expressed in the same bacterial cell, either from the same vector, or from different compatible vectors simultaneously present. The libraries are cloned into the expression vector or vectors as in the basic method, but so that sequences encoding different affinity 'tags' are attached to the fragments encoded by the different DNA libraries. As in the basic method, bacterial cells are lysed and filtered, and contacted with affinity media that is specific to the (primary) affinity tag attached to only one library to select for soluble, folded and unaggregated protein fragments. As in the basic method protein levels are assayed by ELISA or immunoblot, but using antibodies directed against the (secondary) affinity tag (or tags) attached to the other library (or libraries). Strong signals against a secondary tag, will indicate the presence of a fragment expressed from one library, that was efficiently transported by and formed a stable non-aggregated complex with a fragment from the primary library whose 'tag' was utilised for selection.

In a further aspect, the methods described herein may be combined to provide a method of producing a library of nucleic acid fragments, the nucleic acid fragments encoding one or more portions of a polypeptide, and identifying fragments encoding soluble protein domains, the method comprising:

amplifying a nucleic acid sequence encoding the polypeptide in the presence of a non-native nucleotide so that the non-native nucleotide is incorporated into the amplified product nucleic acid sequence at a frequency related to the relative amounts of the non-native nucleotide and its corresponding native nucleotide, if present;

contacting the product nucleic acid sequence with one or more reagents capable of recognising the presence of the non-native nucleotide and cleaving the product nucleic acid sequence or excising the non-native nucleotide, thereby producing nucleic acid sequences encoding fragments of the polypeptide;

expressing a library of the nucleic acid fragments to produce the protein domains encoded by the fragments, wherein the protein domains are expressed as fusions with an affinity tag; and separating soluble proteins using the affinity tag.

Embodiments of the present invention will now be described in more detail by way of example and not limitation with reference to the accompanying figures.

BRIEF DESCRIPTION OF THE FIGURES

FIG. 1 shows a representation of the fragmentation of a single molecule of PCR product with a low level of dUTP incorporated. Since the position at which the dUTP is incorporated is different in different PCR product molecules, the position at which cleavage occurs is different and will therefore result in sampling of all possible positions in a particular coding sequence. A library of DNA fragments are therefore produced that sample all possible positions representing all possible fragments within a certain size range, that is determined by the ratio of dUTP:TTP used in the initial amplification reaction.

DETAILED DESCRIPTION

Introduction

We have developed a method for identification of protein domains comprising two main steps: 1) production of a library of expression vectors that contain DNA fragments of defined size range that have been sampled essentially randomly from a particular target coding sequence; 2) screening of the library for clones that express soluble protein domains. The first step employs an enzymatic fragmentation method based on the DNA base-excision repair pathway and the second step makes use of a protein purification method that is selective for soluble protein domains over insoluble protein fragments. The two key novel aspects of the methodology have been tested in two separate pilot feasibility studies: one involving the novel gene fragmentation aspects of the technology and another involving testing of the selectivity of the protein purification method for soluble proteins with tertiary structural integrity. These studies demonstrate that the DNA fragmentation method is efficient and reproducible, generating blunt-ended DNA fragments suitable for cloning. In addition, the fragment size range produced is found to be reproducible and solely a function of the ratio of dUTP:TTP used in the amplification of the PCR product. In a second aspect, these studies show the present protein purification method to be highly selective for soluble vs. insoluble protein and therefore suitable for screening of libraries of clones in order to identify those that produce soluble protein domains.

Materials and Methods

PCR

Initially four coding sequences were identified as potential targets for application of the "Domain hunting" method: human BRCA2 exon 11, yeast elongation initiation factor 2, Dengue virus type 1 NS5 and the N-SH2-Inter-SH2-C-SH2 region of the human signal transduction protein p85. Oligonucleotide primers were designed and synthesised for PCR amplification of each coding sequence. PCR was then performed using Taq DNA polymerase according to the manufacturers instructions except that dGTP, dCTP, DATP were used at a concentration of 200 µM each, and TTP and dUTP were used at a concentration of 198 µM and 2 µM respectively. PCR was therefore performed in the presence of a ratio of 99% TTP to 1% dUTP allowing incorporation of dUTP at an average of ~1% at any particular thymidine nucleotide position in the sequences. Thirty cycles of PCR were performed for each template and an annealing temperature 5° C. below the theoretical melting temperature was used for each reaction. The extension time used for each reaction was 60 seconds per kilobase of full-length product.

Fragmentation of PCR Products

Figure 1:
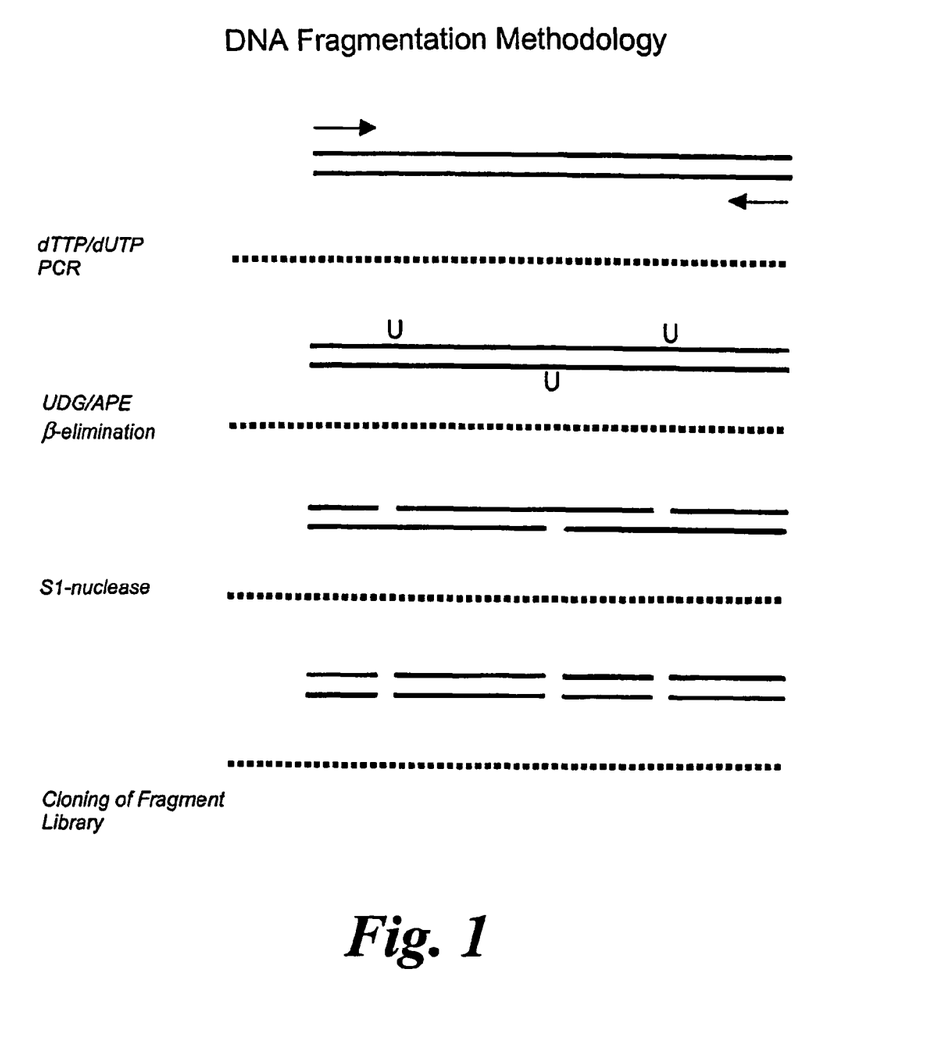
Figure 2:
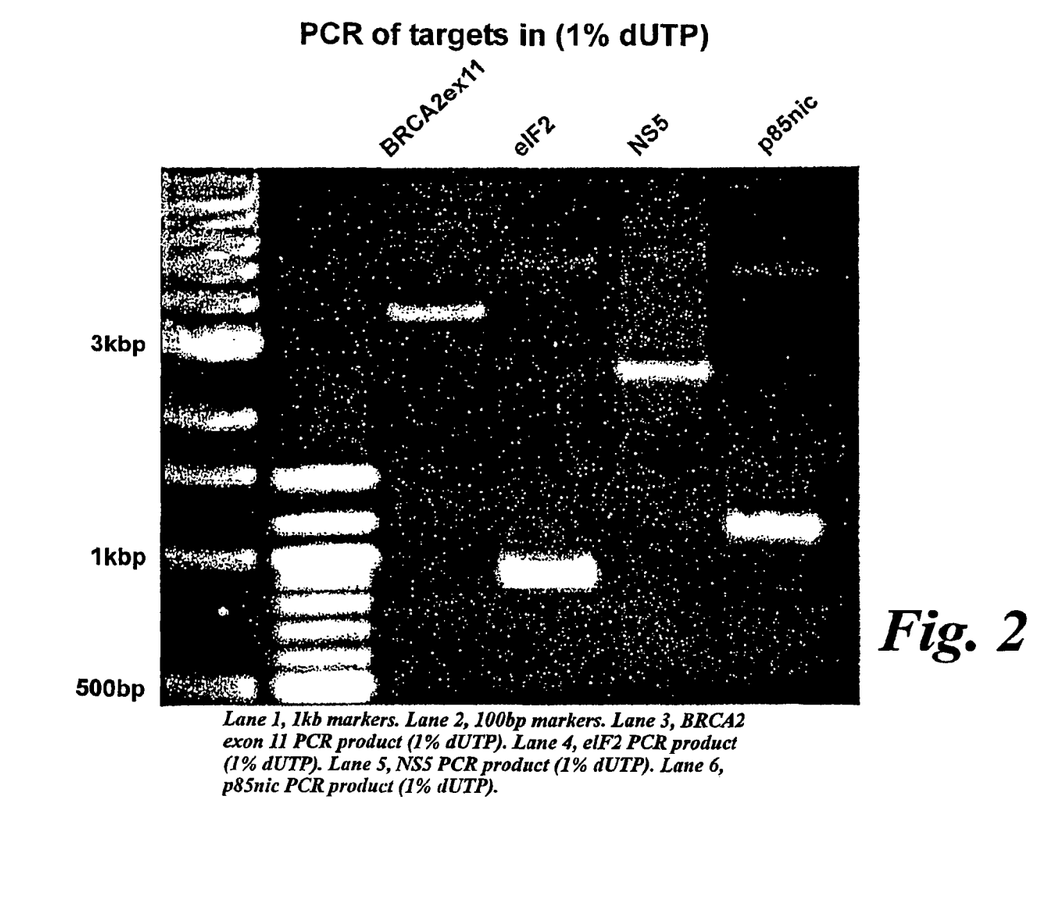
FIG. 2 shows a gel showing the nucleic acid fragments produced when the method described herein was applied to exon 11 of BRCA2, eIF2, NS5 and p85nic.

Digestion with UDG and APE Enzymes:

The fragmentation protocol is summarised in FIG. 1. The above NS5 and p85nic PCR products were treated with UDG (New England Biolabs. Inc.) and APE enzymes as below. Nth and NFO were over-expressed in *E. coli* and purified to homogeneity. Two different APE enzymes were assessed for their cleavage efficiency, NFO and Nth.

PCR products were purified by agarose gel electrophoresis and gel extraction according to the manufacturer's instructions (Qiagen Inc.) and then incubated with 1U of UDG per microgram of DNA and 2 µl of 2 µg/µl APE (either Nth or NFO) per microgram of DNA at 37° C. for 60 mins. Spermine tetrahydorchloride (Calbiochem Inc.) was then added to 0.2 mM final concentration before incubating at 37° C. for 30 mins and then 70° C. for 15 mins and 4° C. 2 mins. The product was then purified (PCR purification kit, Qiagen Inc.) and the purified DNA eluted in 1 mM Tris.HCl pH8.0. The product was then incubated with 1 unit of S1-nuclease per microgram of DNA at 37° C. for 60 mins. The product was then purified by 1% agarose gel electrophoresis and a block of gel corresponding to DNA products of 300-600 bp was excised and purified by gel extraction as above. The above product was then treated with shrimp alkaline phosphatase using one unit of enzyme per microgram of DNA at 37° C. for one hour before adding the same quantity of fresh enzyme and incubating for a further hour. The reaction was then heated to 65° C. for 15 minutes to totally inactivate the alkaline phosphatase. The product was then purified (PCR purification kit, Qiagen Inc.) and the purified DNA eluted in 1 mM Tris.HCl pH8.0. This DNA was then used for blunt-end cloning as described below. Alternatively, for TA cloning using the pCRT7-NT-TOPO vector (Invitrogen, Inc.) a final incubation with Taq DNA polymerase was performed to add single adenine nucleotide to the 3' ends of the products. This was performed by incubating the product for 15 minutes at 72° C. in the presence of a conventional PCR reaction mixture, well known to those skilled in the art, but without primers.

Cloning of the DNA Fragments

~100 ng of the above fragmented p85nic coding sequence was cloned using three different vectors (pCRBlunt, pCR4Blunt-TOPO and pCRT7-NT-TOPO) according to the manufacturer's protocol (Invitrogen Inc.). The transformation reactions were plated onto LB agar plates containing either ampicillin (pCRT7-NT-TOPO) or kanamycin (pCRBlunt, pCR4Blunt-TOPO) depending on the vector used for transformation.

Analysis of Clones

Plasmid minipreps were performed (Qiagen inc.) for ~40 clones derived from pCRT7-NT-TOPO/p85 fragment transformations and for ~20 clones derived from pCRBluntTOPO and ~20 clones derived from pCRBlunt. pCRT7-NT-TOPO/p85 fragment derived plasmids were digested with EcoR1 and BamHI (New England Biolabs Inc.) and analysed by 1% agarose gel electrophosesis.

Plasmid samples were DNA sequenced using the Cambridge University Biochemistry Dept. DNA sequencing service and results analysed using Vector NTI (Informax Inc.).

Selective Purification of Folded Protein 50 ml cultures of *E. coli* BL21(DE3) cells expressing soluble C-terminal domain of Sti1 (cSti1) (REF), or insoluble Gsk3 (full length and catalytic domain) (REF) were pelleted and resuspended in 5 ml of lysis buffer (50 mM $NaH_2PO_4$, 300 mM NaCl, 1 mM imidazole pH 8.0). 1 mg ml$^{-1}$ lysozyme and 10 µg of Rnase A were added and the lysate incubated on ice for 30 min. 0.5 ml of the lysate was then passed through a Qiagen TurboFilter (8 strip) as described by the manufacturer (Qiagen Inc.). 200 µl of the cleared lysates were added to 20 µl of Ni-NTA magnetic beads in 96 well microtitre plates. The plates were then shaken for 60 min, the beads washed twice in lysis buffer containing 10 mM imidazole, and bound protein eluted with 50 µl lysis buffer containing 300 mM imidazole. 20 µl aliquots of the whole cell extract, the turbo-filtered extract and eluate from the beads was analysed by SDS-PAGE.

Results

DNA Fragmentation Trials

We have performed computer modelling experiments to predict the size of fragments that would be produced by the present DNA fragmention method for different levels of dUTP incorporation. These predicted that 1% dUTP incorporation would produce a fragment size range with a distribution centering around 500 bp. Four different coding sequences ranging in size from ~1-3.1 kb were therefore amplified by PCR using Taq DNA polymerase in the presence of 1% dUTP demonstrating that PCR is highly efficient under these conditions (FIG. 2).

Figure 3:
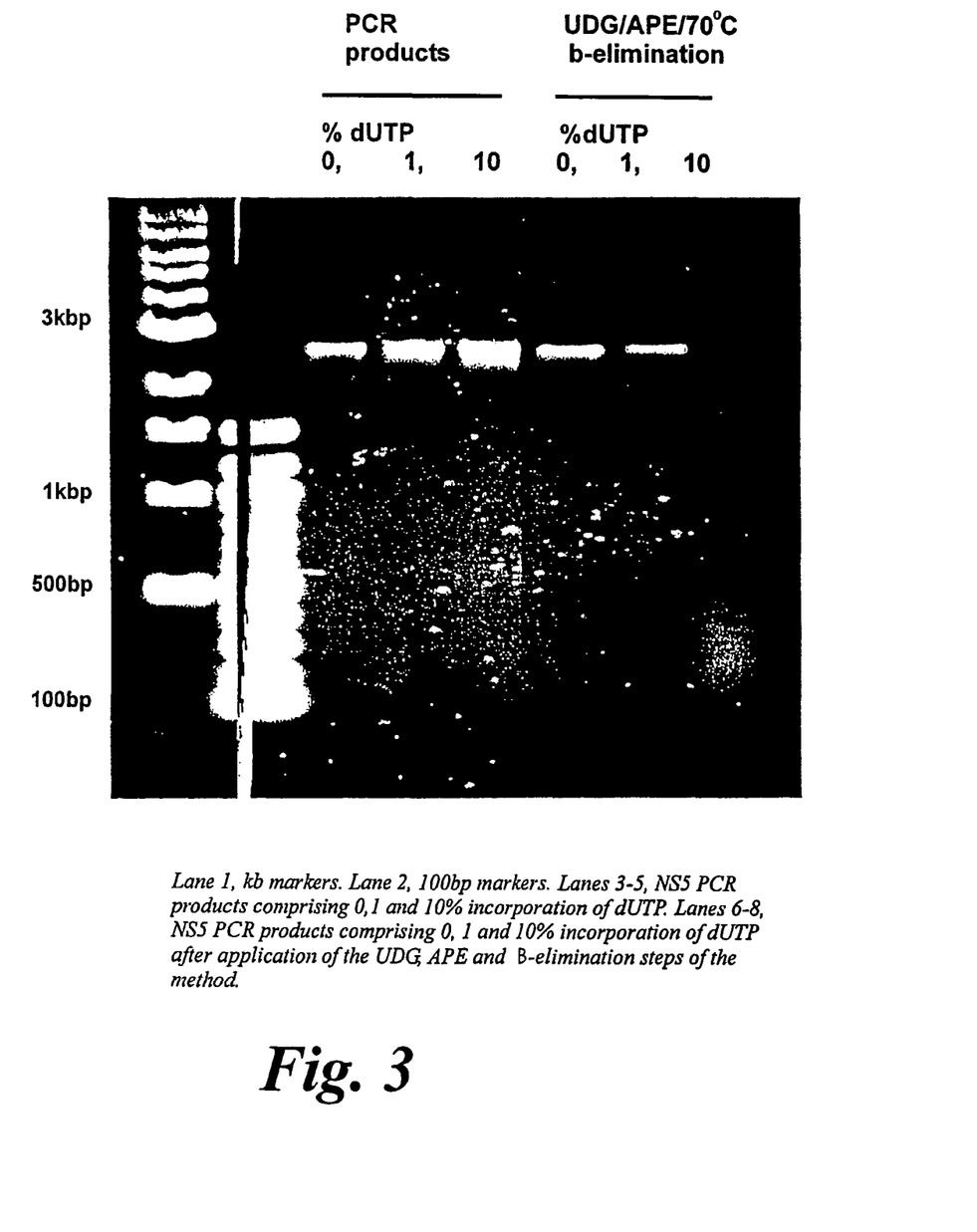
FIG. 3 shows the effect of UDG, APE and β-elimination treatment on NS5 PCR products comprising different levels of dUTP incorporation.

We have then compared NS5 PCR products amplified using different ratios of TTP:dUTP (100:0, 99:1 and 90:10) by treatment with UDG and APE and β-elimination (FIG. 3). This indicates that as expected the PCR products with no dUTP incorporated are unaffected by this treatment while 1% dUTP products show some slight evidence of fragmentation and 10% dUTP products show considerable evidence of fragmentation. These results are as expected since this treatment of 1% dUTP products with UDG and APE and β-elimination should introduce single stranded one nucleotide gaps in the dsDNA at ~500 bp intervals on average. Similarly treatment of 10% dUTP products should produce gaps at intervals of around 50 bp on average. On agarose gel electrophoresis therefore the 1% dUTP products would migrate in essentially the same way as uncut 100% TTP products since the 65° C. 15 minute incubation step used for β-elimination would not be expected to cause significant melting of strands with 500 bp overlaps between single-nucleotide gaps. The 10% dUTP product would however be expected to have melted significantly and then reannealed to produce a mixture of smaller annealed products consistent with that observed.

Figure 4:
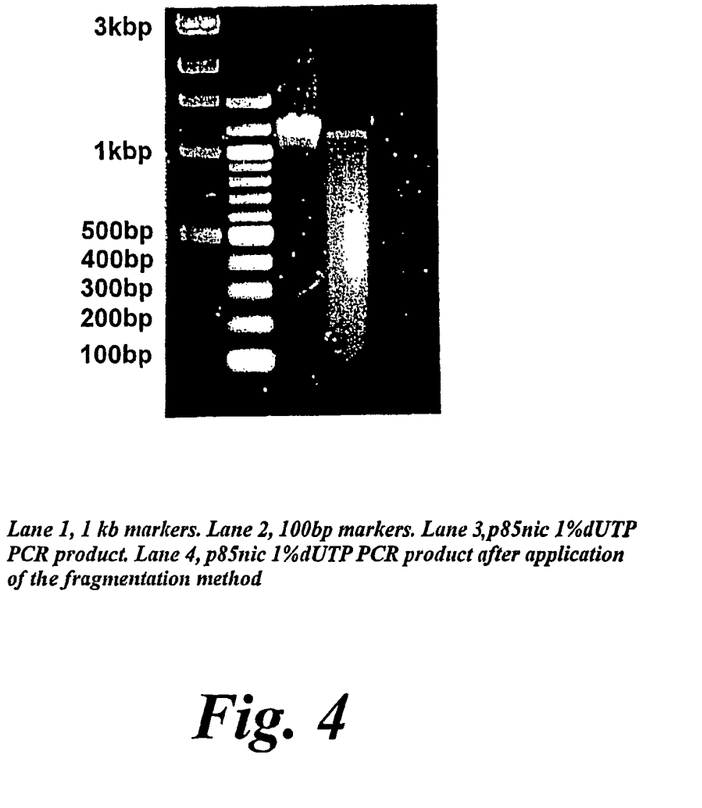
FIG. 4 shows the PCR product produced after amplification of p85nic with 1% dUTP before and after fragmentation.

The whole fragmentation method (FIG. 1) has been applied to 1% dUTP p85nic PCR product (FIG. 2). This has been repeated using different APE enzymes and with different lengths of incubation always yielding the same size distribution of product ranging from ~100 bp to 1.2 kb with maximum band intensity centred around 500 bp as predicted (FIG. 4). This process has been scaled up reproducibly for fragmentation of ~10 µg of DNA, indicating that generation of quantities of product sufficient for production of large libraries of clones according to the present invention is feasible.

Cloning

Transformation of E. coli cells with p85nic fragment cloning reactions was successful using three different cloning approaches: pCRBlunt ligation; pCR4Blunt-TOPO cloning; and pCRT7-NT-TOPO cloning. TOPO cloning of fragmented p85nic insert DNA into both pCR4Blunt-TOPO and pCRT7-NT-TOPO produced around 250 colonies per 100 ng of insert used. Blunt-end ligation of fragmented p85nic DNA to pCR-Blunt produced ~1000 colonies at 16° C. and 120 colonies at 37° C. per 100 ng of fragmented DNA. These results indicate that a substantial proportion of the DNA fragments produced as described are blunt ended as expected. Cloning of DNA fragments produced by the method using the above cloning methods is therefore of sufficiently high efficiency to allow generation of libraries of thousands of clones.

Characterisation of Cloned p85nic Fragments

Figure 5:
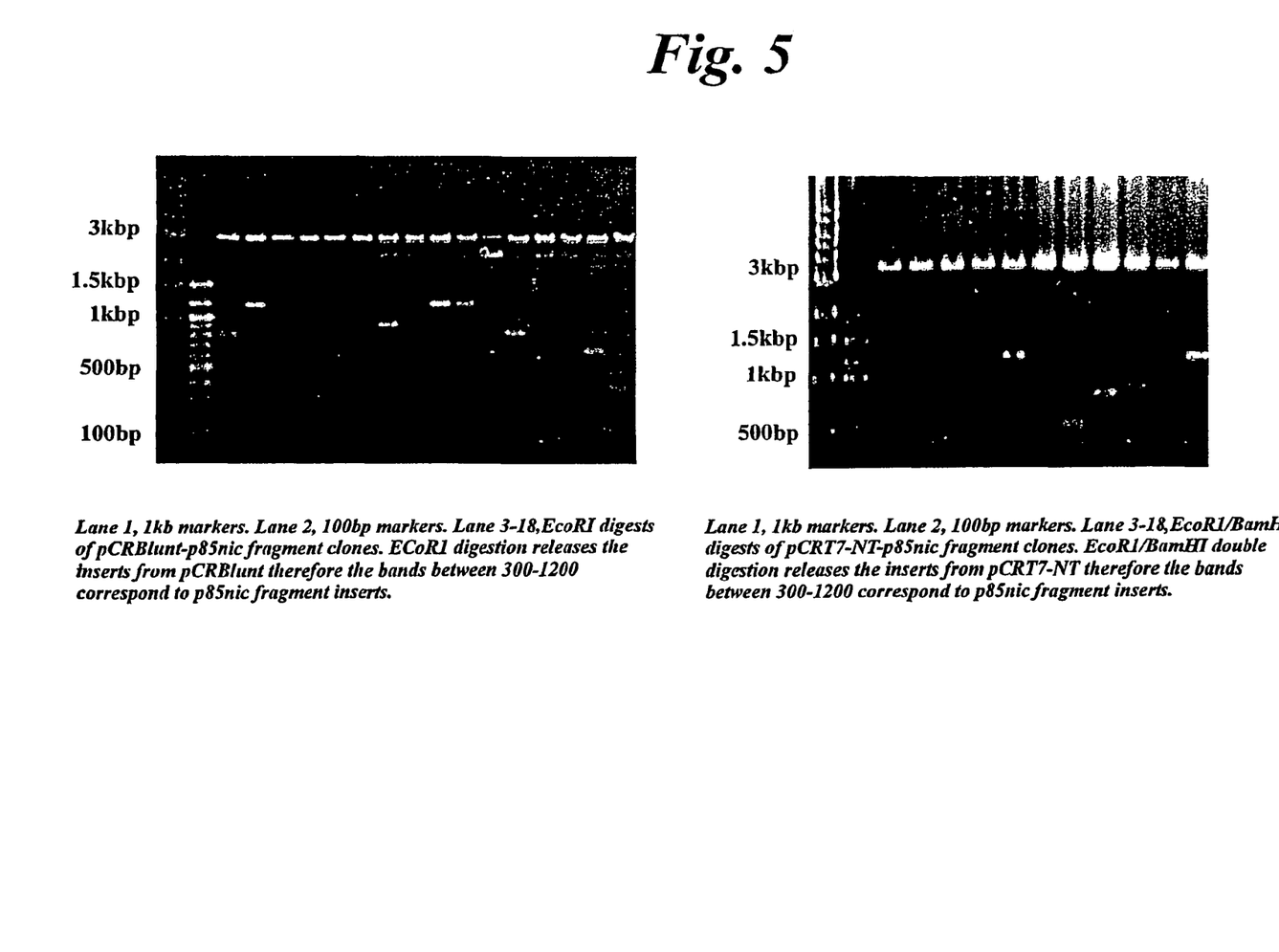
FIG. 5 shows agarose gel electrophoresis of restriction digests of pCRBlunt/p85nic fragment clones and pCRT&-NT/p85nic fragment clones.

Restriction characterisation of plasmid DNA derived from clones generated by both TOPO cloning and blunt end ligation indicated that >90% of clones contained an insert and the distribution of the sizes of inserts correlated closely with the size range of p85nic DNA fragments used for cloning (FIG. 5). DNA sequencing of the cloned DNA inserts suggests that the fragments appear to be sampled in an essentially random manner from the p85nic coding sequence. No nucleotide substitutions have yet been detected by DNA sequencing, indicating that as expected the method is not inherently mutagenic. DNA sequencing of a large number of clones is necessary in order to accurately measure the randomness of sampling, frequency of mutation.

Selective Purification of Folded Protein

Figure 6:
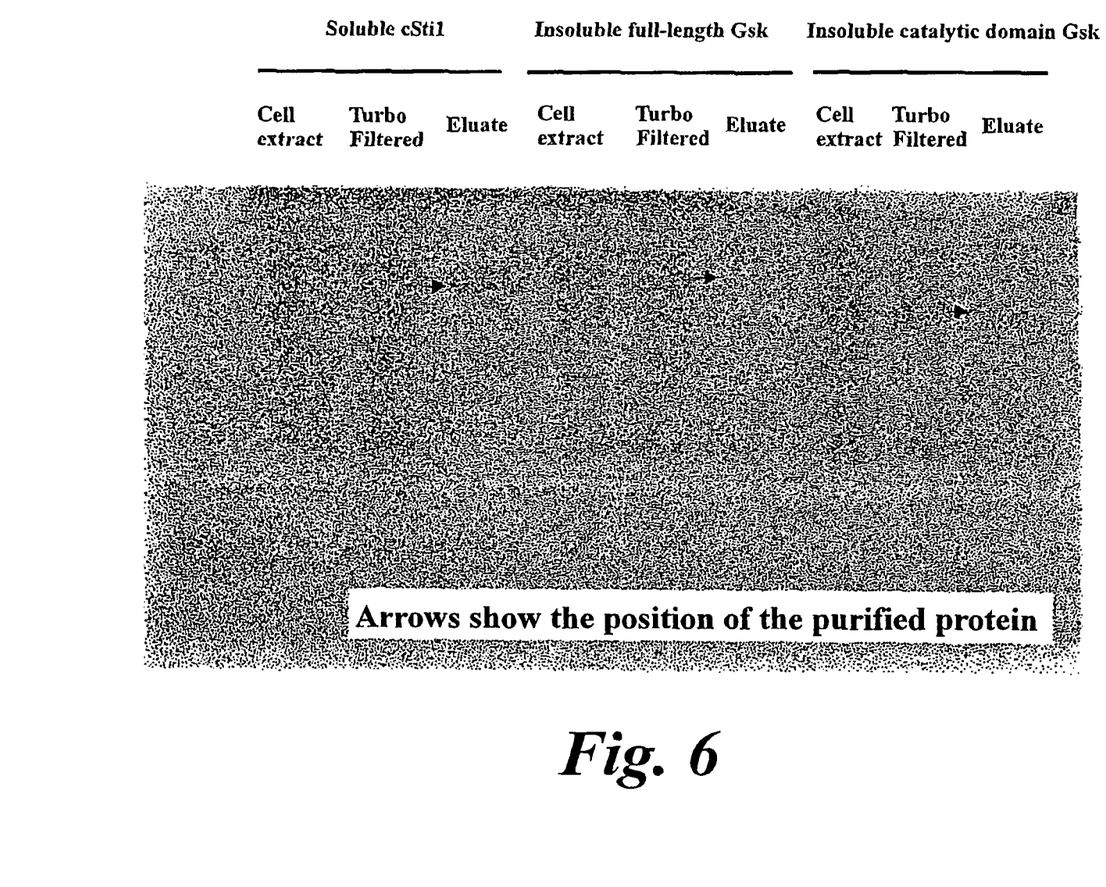
FIG. 6 shows the analysis of the selectivity of the purification method for soluble vs insoluble protein. Samples of cell extract, Turbo-filtered cell extract And Ni-NTA eluate from purification trials of soluble cStil, insoluble full length Gsk and the insoluble catalytic domain of Gsk were run on SDS-PAGE.

In order to assess the selectivity of the purification method for folded protein versus unfolded or aggregated protein we have applied the purification method to a set of well-characterised proteins with known solubility properties. Cultures of E. coli BL21 (DE3) cells expressing soluble C-terminal domain of Sti1 (cSti1), or insoluble Gsk3 (full length and catalytic domain) were harvested and the cells lysed enzymatically before passing through a Qiagen TurboFilter as described by the manufacturer (FIG. 6). This step cleared the cell lysates and significantly reduced the amount of the insoluble Gsk in the lysate, but did not effect the level of the soluble cSti1. Further reduction of the quantity of insoluble constructs was seen following Ni-NTA magnetic bead purification. The cleared lysates were then purified using Ni-NTA magnetic beads in 96 well microtitre plates. The whole cell extract, the turbo-filtered extract and the Ni-NTA eluate were then analysed by SDS-PAGE showing that the recovery of the soluble cSti1 is at least 100 times more efficient than the insoluble constructs. The difference in the level of recovery of soluble vs. insoluble recombinant protein demonstrates that this purification method is highly selective for soluble folded protein over insoluble/misfolded protein over a wide dynamic range. This purification approach will therefore allow sensitive detection of soluble folded protein fragments or domains over insoluble misfolded fragments and therefore allow identification of regions of protein sequence that correspond to folded protein.

CONCLUSIONS

The gene fragmentation study provided verification of incorporation of dUTP into the target gene by PCR, fragmentation of the target gene, robust control of the range of fragment sizes generated and efficicnet cloning of the fragments. We have tested the efficiency of PCR in the presence of dUTP for four different coding sequences. We have then compared the behaviour of PCR products prepared in the presence of different ratios of TTP:dUTP by treatment with uracil DNA glycosylase (UDG) and two different apurinic/apyrimidinic endonucleases (APE). This demonstrated that fragmentation occurs only to uracil containing PCR products and that the size of the fragments produced corresponds directly to the dUTP:TTP ratio used in the PCR amplification step. We selected the p85nic coding sequence for further analysis by the above enzymes and also for subsequent treatment with spermine and S1 nuclease. This demonstrated that fragments of p85nic of the size range predicted in theory for 1% dUTP incorporation were indeed produced. This also showed that as predicted these fragments were blunt ended since they could be cloned efficiently by blunt end cloning methods. A method for identification of soluble protein fragments or domains that can be efficiently expressed and purified from bacteria has been established and validated using several targets of well-characterised solubility properties. Coupling of the DNA ragmentation/cloning aspects with the soluble protein domain identification aspects of the method therefore provides a holistic method for generation of vectors for high-level soluble expression of newly discovered protein domains. These vectors can then be used directly for production of large quantities of soluble protein domains for structural and functional studies, without the need for any subsequent genetic manipulation or optimisation of protein expression or purification.

REFERENCES

The references cited herein are all expressly incorporated by reference.

Cohen, S. L. (1996) Structure 4 (9), 1013-1016. Finucane, M. D., Tuna, M., Lees, J. H. and Woolfson (1999) *Biochemistry*, 38, 11604-11612.

Kawasaki, M. and Inagaki, F. (2001) *Biochem. Biophys. Res. Commun.* 280 (3), 842-844.

Moriki, T., Kuwabara, I., Liu, F. T. and Maruyama, I. N. (1999) *Biochem. Biophys. Res. Commun.* 265 (2), 291-296.

Sambrook J, Fritsch, E F, Maniatis, T (1989) *Molecular Cloning: A Laboratory Manual*, $2^{nd}$ ed, pp 5.33-5.86.

Savva, R, McAuley-Hecht, K, Brown, T, Pearl, L H (1995) *Nature*, 373, 487-493.
Savva, R, Pearl, L H (1995) *Nature Structural Biology*, 2, 752-757.
Panayotou, G, Brown, T, Barlow, T, Pearl, L H, Savva, R (1998) *J Biol Chem*, 273, 45-50.
Barrett, T E, Savva, R, Panayotou, G, Barlow, T, Brown, T, Jiricny, J, Pearl, L H (1998) *Cell*, 92, 117-129.
Barrett, T E, Schärer, O D, Savva, R, Brown, T, Jiricny, J, Verdine, G L, Pearl, L H (1999) *EMBO J*, 18, 6599-6609.
Greagg, M A, Fogg, M J, Panayotou, G, Evans, S J, Connolly, B, Pearl, L H (1999) *Proc Natl Acad Sci*, 96, 9045-9050.
Bailly V, Verly W G (1989) *Biochem. J.* 259, 761-768.
Wigley, W. C., Stidham, R. D., Smith, N. M., Hunt, J. F. and Thomas, P. J. (2001) *Nature Biotechnology* 19 (2) 131-136.

The invention claimed is:

1. A method of screening for soluble domains in a protein of interest comprising producing a library of nucleic acid fragments, each nucleic acid fragment encoding a fragment of said protein comprising one or more protein domain portions, and identifying fragments in the library encoding a soluble protein domain or a soluble fragment of said protein comprising more than one protein domain, the method comprising:
   a) amplifying a nucleic acid sequence encoding said protein in the presence of a known amount of non-native nucleotide, with or without a known amount of a native nucleotide corresponding to said non-native nucleotide, thereby resulting in an amplified product nucleic acid sequence, the non-native nucleotide being incorporated into the resulting amplified product nucleic acid sequence at a frequency related to the known amounts of said non-native nucleotide compared to the known amount of said native nucleotide, if present;
   b) producing nucleic acid fragments of between 100 and 1500 nucleotides from said amplified products for ligation into an expression vector in a method consisting of contacting said amplified product nucleic acid sequence of step a) with one or more reagents which recognize the presence of the non-native nucleotide and cleave the amplified product nucleic acid sequence or excise the non-native nucleotide, thereby producing nucleic acid fragments of between 100 and 1500 nucleotides each encoding a fragment of said protein having one or more domain portions suitable for ligation into an expression vector;
   c) ligating each nucleic acid fragment of between 100 and 150 nucleotides from step b) into an expression vector, thereby producing a library of expression vectors;
   d) expressing the library of said nucleic acid fragments from step c) to produce protein domains encoded by said nucleic acid fragments, wherein the protein domains are expressed as fusions with a C-terminal affinity tag which is less than 15 amino acid residues in length;
   e) separating soluble fusion protein domains from insoluble protein domains using the affinity tag to identify soluble protein domains, thereby identifying fragments in the library encoding soluble protein domains; and
   f) identifying soluble protein domains obtained in step e) as domains of the protein of interest by protein sequencing.

2. The method of claim 1, wherein the step of amplifying the nucleic acid sequence is effected by PCR using a non-native deoxynucleotide, either alone or in a mixture of the non-native and native nucleotide.

3. The method of claim 2, wherein the non-native nucleotide is uracil or 3-methyl adenine.

4. The method of claim 1, wherein the nucleic acid sequence to be amplified is present in a cDNA library, a RNA library or a sample of genomic DNA.

5. The method of claim 1, wherein the nucleic acid fragments encoding said one or more portions of the polypeptide are between 200 and 1200 nucleotides in length.

6. The method of claim 1, wherein said contacting of the amplified product nucleic acid sequence with one or more reagents produces fragments on average about every second nucleotide.

7. The method of claim 1, wherein the at least one reagent which recognizes and cleaves the amplified product nucleic acid sequence at the non-native nucleotide comprises at least one enzyme which can recognise the presence of the non native nucleotide and cleave the nucleic acid sequence at or around the incorporated non-native nucleotide.

8. The method of claim 7, wherein the at least one enzyme includes a DNA glycosylase and an endonuclease.

9. The method of claim 8, wherein the non-native nucleotide is deoxyuracil, the endonuclease is apurinic/apyrimidinic endonuclease (APE), and the glycosylase is uracil-DNA glycosylase (UDG).

10. The method of claim 1, wherein the protein domains expressed from the library of nucleic acid fragments comprise a constant portion and a portion generated by the amplifying and contacting steps.

11. The method of claim 1, further comprising transforming host cells with the expression vectors to produce a library of host cells capable of expressing fragments of the polypeptide.

12. The method of claim 11, further comprising expressing the nucleic acid sequences encoding fragments of the polypeptide and optionally isolating the polypeptide fragments thus produced.

13. The method of claim 1, wherein the nucleic acid fragments comprise a nucleic acid sequence encoding a protease cleavage site which is included in the expressed polypeptide fragments.

14. The method of claim 1, wherein the polypeptide fragments are expressed to include an affinity tag.

15. The method of claim 1, wherein the affinity tag is polyhistidine, a Flag or Glu epitope, a S-tag, calmodulin binding peptide or ribonuclease S.

16. The method of claim 15, wherein the affinity tag is a $His_6$-tag.

17. The method of claim 11, further comprising releasing the soluble protein domains from the cells.

18. The method of claim 17, wherein the step of releasing the soluble protein domains is carried out under non-denaturing conditions.

19. The method of claim 18, wherein the non-denaturing conditions comprise using enzymes or non-denaturing detergents.

20. The method of claim 11, further comprising filtering out unbroken cells, cell debris and insoluble material.

21. The method of claim 11, further comprising clarifying cell lysate by centrifugation.

22. The method of claim 11, further comprising purifying cells transformed with different proteins in parallel by affinity chromatography.

23. The method of claim 1, wherein the step of separating the soluble protein domains is carried out by contacting the produced protein domains with a solid phase having a binding partner of the affinity tag immobilised thereon.

24. The method of claim 23, wherein the binding partner is:
   (a) metal ions such as $Ni^{2+}$ or $Co^{2+}$ for binding a polyhistidine affinity tag; or (b) anti-Flag antibodies for binding a Flag or Glu epitope affinity tag; or
(c) streptavidin for binding a S-tag affinity tag; or
(d) calmodulin in the presence of $Ca^{2+}$ for binding a calmodulin binding peptide affinity tag; or
(e) aporibonuclease S for binding a ribonuclease S affinity tag.

25. The method of claim 1, further comprising assaying for the presence of soluble protein domains.

26. The method of claim 25, wherein the step of assaying is carried out using at least one of anti-tag ELISA, SDS-PAGE or LC-ESI-MS.

27. The method of claim 25, wherein the step of assaying for the soluble protein domains comprises quantifying a protein expression level of at least one of the protein domains.

* * * * *